United States Patent [19]

Aida et al.

[11] Patent Number: 4,986,259
[45] Date of Patent: Jan. 22, 1991

[54] APPARATUS AND METHOD FOR DISINTEGRATING CALCULUS

[75] Inventors: Satoshi Aida; Nobuyuki Iwama, both of Kanagawa, Japan

[73] Assignee: Kabushiki Kaisha Toshiba, Kanagawa, Japan

[21] Appl. No.: 317,531

[22] Filed: Mar. 1, 1989

[51] Int. Cl.$^5$ .............................................. A61B 17/22
[52] U.S. Cl. ............................... 128/24 A; 128/660.03
[58] Field of Search ................ 128/328, 24 A, 660.03, 128/24 EL, 24 AA; 606/128

[56] References Cited

U.S. PATENT DOCUMENTS

| | | | |
|---|---|---|---|
| 4,610,249 | 9/1986 | Makofski et al. | 128/24 EL |
| 4,617,931 | 10/1986 | Dory | 128/24 EL |
| 4,658,828 | 4/1987 | Dory | 128/660.03 |
| 4,696,299 | 9/1987 | Shene et al. | 128/660.03 |
| 4,763,652 | 8/1988 | Brisson et al. | 128/24 A |
| 4,771,787 | 9/1988 | Wurster et al. | 128/24 A |
| 4,787,371 | 11/1988 | Grasser et al. | 128/328 |
| 4,803,995 | 2/1989 | Ishida et al. | 128/328 |
| 4,819,621 | 4/1989 | Ueberle et al. | 128/328 |
| 4,834,074 | 5/1989 | Reichenberger | 128/24 A |

FOREIGN PATENT DOCUMENTS 3543096 6/1986 Fed. Rep. of Germany ...... 128/328
3621935 1/1988 Fed. Rep. of Germany ...... 128/328

Primary Examiner—Lee S. Cohen
Assistant Examiner—John D. Zele
Attorney, Agent, or Firm—Banner, Birch, McKie & Beckett

[57] ABSTRACT

This invention relates to an apparatus for disintegrating calculus having a main ultrasonic transducer for emitting a high power ultrasonic shock wave to disintegrate a kidney stone in a patient, and for emitting a weak ultrasonic shock wave, before emitting the high power ultrasonic shock wave. A sound receiver receives sounds generated by the patient's body in response to the weak ultrasonic shock wave, and converts the sounds into electrical signals. A kidney stone confirming circuit receives electrical signals from the sound receiver and determines whether the kidney stone is positioned at the focal point of the main transducer. The apparatus prevents the emission of the high power ultrasonic shock wave when the position of the kidney stone is not coincident with the focal point of the main transducer in order to prevent any harm to the patient's normal tissue.

11 Claims, 2 Drawing Sheets

APPARATUS AND METHOD FOR DISINTEGRATING CALCULUS

TECHNICAL FIELD

This invention relates to an apparatus and method for noninvasive treatment of human body concretion or calculus using shock wave energy and more particularly to an apparatus and method for accurately and reliably confirming the location of calculus using audio sounds.

BACKGROUND OF THE INVENTION

Recently, lithotrity apparatus for disintegrating calculus or kidney stones using high power pulsed ultrasonic wave (hereinafter referred to as ultrasonic shock wave) has attracted attention, because it has advantages in size and cost as compared to previous lithotrity apparatus of the type shown, for example, in U.S. Pat. No. 4,610,249, using other types of shock wave energy. A lithotrity using ultrasonic shock wave is shown, for example, in U.S. Pat. No. 4,617,931.

A lithotrity using ultrasonic shock wave, hereinafter referred to as an ultrasonic lithotrity, generally comprises a main ultrasonic transducer having a spherical surface with a focal point formed at its geometric center for disintegrating calculus, and an imaging ultrasonic transducer or other imaging device for generating a cross-sectional image of a patient, disposed at a distance from the main ultrasonic transducer. Once the focal point of the main ultrasonic transducer is positioned on the calculus using the image generated by the imaging transducer, a high power ultrasonic shock wave is transmitted to the calculus from the main ultrasonic transducer to destroy the calculus.

One problem with this apparatus is that it is extremely difficult to precisely locate the focal point of the main ultrasonic transducer on the calculus using only the cross-sectional image. Further, transmission of the high power ultrasonic shock wave must usually be repeated a number of times to completely disintegrate the calculus. Thus, even if the focal point is initially positioned at the calculus, the patient may move during the period between successive transmissions of high power shock wave so that the calculus is shifted away from the focal point. As a result, the high power shock wave may be directed toward, and, thus, harm neighboring normal human tissue.

The conventional apparatus depends on the eyesight of the operator to localize the focal point of the main transducer on the calculus, however, other apparatus exists which depends on the auditory sense of the operator. An example of this type of apparatus is shown in Japanese Patent Application (KOKAI) 62-49843. In operation, this apparatus first emits a weak ultrasonic shock wave from the main ultrasonic transducer. The weak ultrasonic shock wave is reflected by the calculus and the resulting echo signal is received back at the main ultrasonic transducer. A detector is provided which selectively detects only those echo signals that are reflected from areas near the focal point of the main ultrasonic transducer. The selected echo signals are then supplied to a loudspeaker which converts the signals into audible sound, so that the operator can then adjust the focal point of the main ultrasonic transducer to the calculus, where the sound is greatest.

This apparatus, however, has several disadvantages. First, because the main ultrasonic transducer must emit both high power and weak ultrasonic shock waves, and also receive echo signals corresponding to the weak ultrasonic shock wave, the apparatus is complicated and large in size. Further, like previous devices, the apparatus depends upon the operator to precisely locate the focal point of the main transducer at the position of the calculus.

SUMMARY OF THE INVENTION

It is an object of this invention to provide an apparatus and method for disintegrating calculus which is easy to operate, and which is small in size and safe for patients.

It is another object of this invention to provide an ultrasonic lithotrity apparatus and method which can efficiently and precisely confirm that the calculus is located at the focal point of the main ultrasonic transducer.

It is still another object of this invention to provide an ultrasonic lithotrity apparatus and method which can prevent the emission of ultrasonic shock wave for disintegrating the calculus when the position of the caculus is not coincident with the focal point of the transducer.

An ultrasonic lithotrity apparatus in accordance with the present invention comprises an ultrasonic transducer having a focal point for transmitting ultrasonic shock waves to a living body, and drive means for driving the ultrasonic transducer to emit first ultrasonic shock waves for confirming that the focal point of the ultrasonic transducer is positioned to coincide with the position of a calculus and to emit second ultrasonic shock waves for disintegrating the calculus. The first ultrasonic shock waves are weak in intensity as compared with the second ultrasonic shock waves.

A microphone is provided to receive sounds from the living body generated in response to the first ultrasonic shock waves, and to convert the sounds into electrical signals. Confirmation means are also provided for confirming that the calculus is positioned at the focal point of the ultrasonic transducer by analyzing the electrical signals from the microphone.

The first ultrasonic shock waves are emitted before every emission of the second ultrasonic shock waves or before every several emissions of the second ultrasonic shock waves.

DETAILED DESCRIPTION OF THE PREFERRED EMBODIMENT

Figure 1:
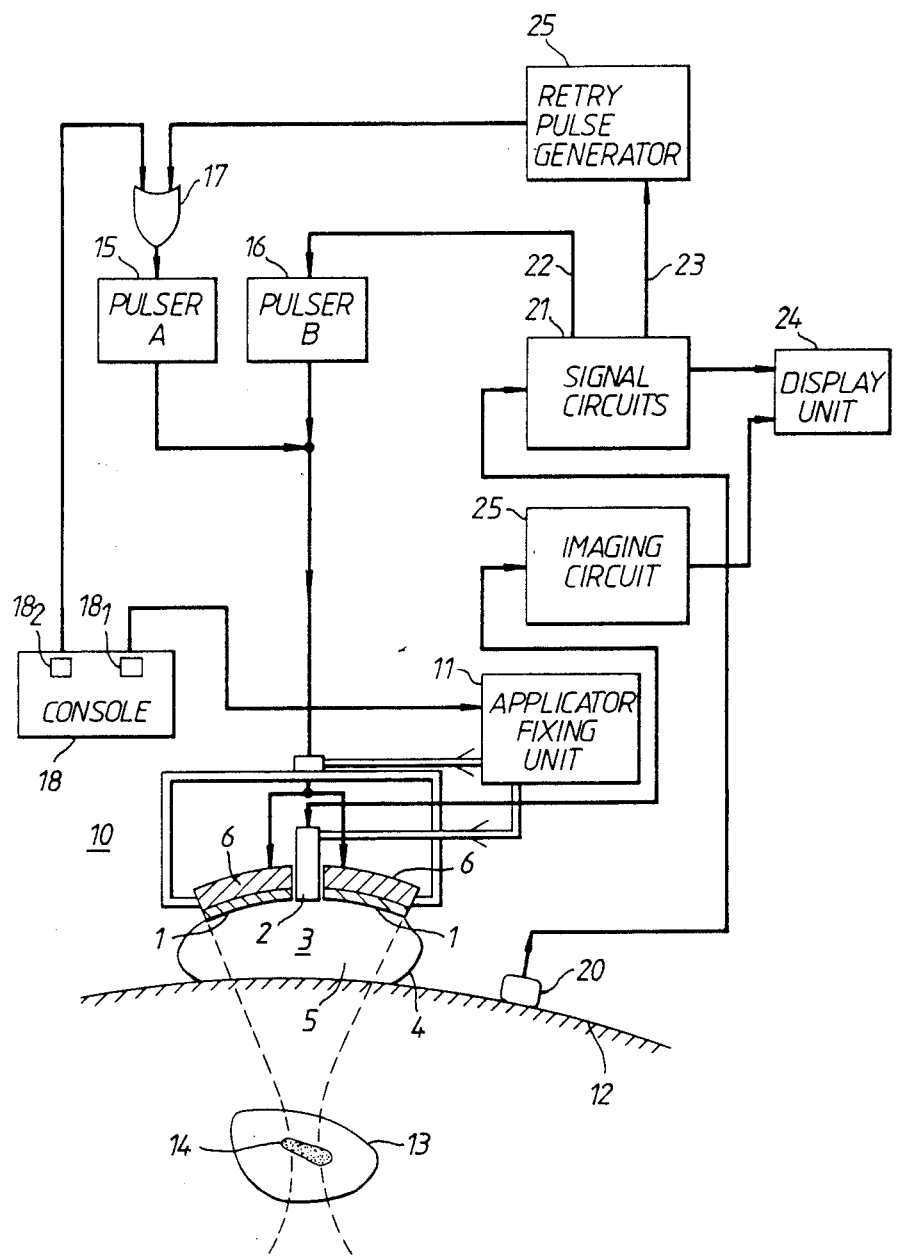
FIG. 1. is a schematic diagram of an apparatus according to a preferred embodiment of the present invention.

FIG. 1 is a schematic diagram of a preferred embodiment of the invention, which is used for disintegrating kidney stones in a patient's kidney.

As shown in the figure, the apparatus comprises an applicator 10 and an applicator fixing unit 11. Applicator 10 comprises a main transducer 1, an imaging transducer 2, an acoustic coupler 3 and a housing 4. Applicator 10 is placed on the patient's back 12 and is positioned using applicator fixing unit 11 so that the geometric focal point of the main transducer 1 coincides with a kidney stone 14 in the patient's kidney 13.

Applicator fixing unit 11 drives imaging transducer 2 to emit ultrasonic waves and to receive echo signals reflected from the patient's body. The echo signals are processed by imaging circuits 25, which are the same as that used in conventional ultrasonic diagnostic apparatus, to create a cross-sectional image of the patient, and the cross-sectional image is displayed at a display unit 24. The relative position of main transducer 1 and imaging transducer 2 is preferably selected so that the focal point of the main transducer is positioned in the cross-sectional plane of imaging transducer 2. An operator can, thus, determine whether a kidney stone coincides with the focal point of the main transducer 1, by observing the cross-sectional image generated by imaging transducer 2.

Main transducer 1 may be a concave piezoelectric transducer with a curvature of 10 cm in diameter and a resonant frequency of 500 kHz, or it may be comprised of a plurality of relatively small piezoelectric transducers arranged in concave surface. A backing member 6 is adhered to the back surface of main transducer 1.

Acoustic coupler 3 comprises a dag 7 filled with water 5, and constructed of a flexible membrane having substantially the same acoustic impedance as water. Acoustic coupler 3 enables an acoustic coupling between main transducer 1 and the surface of the patient's back, so that ultgrasonic shock waves can be efficiently transmitted and received. If desired, an acoustic matching layer may be coated on the surface of the piezoelectric transducer having a thickness of $\lambda/4$, where $\lambda$ is the wavelength of the ultrasonic shock waves, in order to improve efficiency and obtain a short ultrasonic wave.

Pulser A 15 and pulser B 16 are provided to drive main transducer 1. Pulser A 15 supplies a drive pulse having a relatively low voltage so that main transducer 1 emits a weak ultrasonic shock wave for confirming the position of kidney stone 12, and pulser B 16 supplies a high voltage drive pulse to cause main transducer 1 to emit a high power ultrasonic shock wave for disintegrating kidney stone 12. Preferably the energy of the weak ultrasonic shock wave is less than 50% of the energy of the high power ultrasonic shock wave.

Microphone 20 is provided on the patient's back 12, to receive sounds from the patient's body which result when the weak ultrasonic wave impinges on a calculus in the body, and to convert the sound waves into electrical signals. The electrical signals are supplied to signal circuits 21 which determines whether calculus is positioned at the focal point of main transducer 1 by analyzing the electrical signals. When calculus is positioned at the focal point of main transducer 1, signal circuits 21 generates a confirmation signal 22. Confirmation signal 22 is then supplied to pulser B 16, and pulser B 16 drives main transducer 1 to emit a high power ultrasonic shock wave. On the other hand, if calculus is not positioned at the focal point of main transducer 1, signal circuits 21 generates a non-confirmation signal 23.

The process of positioning the focal point of main transducer 1 at the location of a kidney stone is performed as follows. First, the operator generally positions applicator 10 on the patient's back by observing the cross-sectional image of the kidney stone 12 on display unit 24 and manually moving applicator 10 so that the focal point coincides with the kidney stone. If the operator cannot locate the kidney stone in the cross-sectional image, he pushes a positioning switch $18_1$ on a console 18 to supply a positioning signal to applicator fixing unit 11. Applicator fixing unit 11 then generates a driving signal to move applicator 10 in accordance with the positioning signal. Once this adjustment is completed, applicator fixing unit 11 is operated to fix applicator 10 in place.

To explain further, though only a single switch is shown, positioning switch $18_1$ may be one of several switches for controlling the direction of movement, i.e., to the left, to the right, up, down, of applicator 10 and for fixing the applicator in, or releasing the applicator from, a particular position. In use, an operator first releases applicator 10 so that it is free to move. The operator then pushes one of the positioning switches to output a positioning signal to applicator fixing unit 11. Applicator fixing unit 11 responds by moving applicator 10 in accordance with the positioning signal using motor drive mechanisms (not shown) while the switch is being depressed. The operator stops the movenent by releasing the switch when the kidney stone appears on the cross-sectional image. The operator then pushes the fix/release switch to fix the applicator in place.

Once the applicator position is fixed, the calculus confirmation process is executed. The operator begins by pushing switch $18_2$, which generates a control signal which is transmitted to pulser A 15 through OR gate 17. Pulser A 15 then supplies a low voltage drive pulse to main transducer 1, so that main transducer 1 emits a weak ultrasonic shock wave. The weak ultrasonic shock wave penetrates or is reflected by various tissues inside the patient's body. When the weak ultrasonic shock wave contacts a hard material, such as a kidney stone, audio sounds are generated which have a certain frequency dependent upon the material contacted. In the case of kidney stones, the frequency will depend upon the kind and size of the stones. The audio sound waves are received by microphone 20 and are converted to electrical signals which are then supplied to signal circuits 21.

Signal circuit 21 analyzes the eletrical signals from microphone 20 and confirms whether kidney stone 12 is precisely located at the focal point of main transducer 1. If it is, signal circuits 21 outputs a confirmation signal 22 to control pulser B 16 to generate a high voltage drive pulse. The high voltage drive pulse is supplied to main transducer 1 and causes transducer 1 to emit a high power ultrasonic shock wave to disintegrate kidney stone 12.

If, on the other hand, signal circuits 21 determines that kidney stone 12 is not located at the focal point of main transducer 1, signal circuit 21 output a non-confirmation signal 23. When this happens, pulser B 16 is not operated and emission of high power ultrasonic shock waves is not effected. Instead, retry pulse generator 25 is activated, responsive to non-confirmation signal 23, to generate a retry control pulse, which is the same pulse that is generated when switch $18_2$ is pushed. The retry control pulse is supplied to pulser A 15 through OR gate 17. Pulser A 15 then generates a drive pulse to control main transducer 1 to emit a weak ultrasonic shock wave. The calculus confirmation process, described above, is then repeated.

In the preferred embodiment, the calculus confirmation process is executed immediately prior to each operation of transducer 1 to emit high power ultrasonic shock waves. This guards against any harmful effects resulting from the shifting of the position of calculus following the initial localization. If desired, however, the confirmation process could, alternatively, be executed once to confirm the position of the calculus and then repeated after a predetermined number of emissions of high power ultrasonic shock waves.

Figure 2:
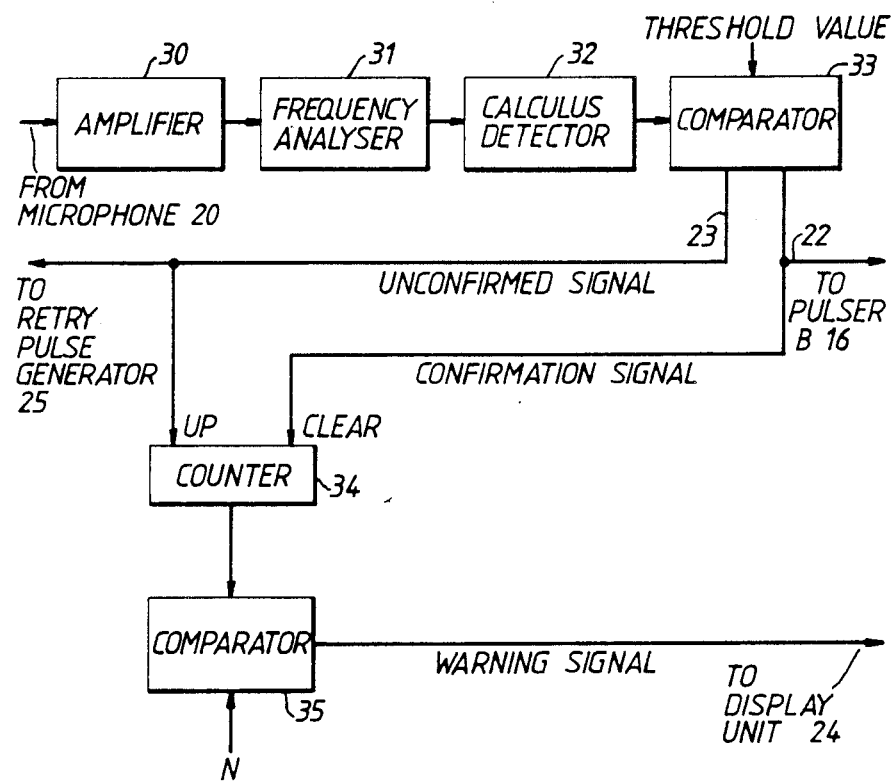
FIG. 2 is a detailed block diagram of the signal circuits 21 shown in FIG. 1.

FIG. 2 is a block diagram of signal circuit 21 shown in FIG. 1. Signal circuit 21 comprises an amplifier 30 which amplifies electrical signals received from microphone 20, a frequency analyzer 31 which extracts only the frequency components corresponding to the inherent frequency of the kidney stone, a calculus detector 32 and a comparator 33. Frequency analyzer 31 may be a band pass filter for passing only the inherent frequency components and calculus detector 32 may be a peak detector or an integrator of the output of frequency analyzer 31. Comparator 33 compares the output of calculus detector 32 with a predetermined threshold value, and generates a confirmation signal 22 when the output of calculus detector 32 is greater than the threshold value and a non-confirmation signal 23 when the output of calculus detector 32 is smaller than the threshold value.

A counter 34 is also provided for counting the number of times the non-confirmation sgnal 23 is generated. Non-confirmation signal 23 is supplied to the UP terminal of counter 34 for counting up the number of times the signal is generated, and confirmation signal 22 is supplied to the CLEAR terminal of the counter 34 to clear the contents of counter 34. The value stored in counter 34 is compared with a predetermined number N, for example N=3, by comparator 35. If non-confirmation signal 23 is generated N times consecutively, comparator 35 generates a warning signal, indicating that an unrecovered or permanent position shift of calculus has occurred or that there is a lack of coincidence between the position of calculus and the focal point of main transducer 1. This warning signal is displayed at display unit 24, so that operator can repeat the localization step using the cross-sectional image.

Though this invention has been descrebed in detail with reference to the preferred embodiment, the invention is not restricted thereo. Thus, for example, the apparatus of the present invention can be utilized for disintegrating not only kidney stones but also other calculus. Further, if the microphone has frequency characteristics such that it only senses the inherent frequency of calculus, the frequency analyzer may be eliminated. The microphone may also be arranged on inside of the applicator, and the described warning signal can, alternatively, be fedback to applicator fixing unit 11 to automatically adjust the position of applicator 10. In addition, the high power ultrasonic shock waves and the weak ultrasonic shock waves can be generated by separate piezoelectric transducers.

We claim:

1. An apparatus for disintegrating a calculus in a living body using ultrasonic shock waves comprising:
   ultrasonic transducer means having a focal point for emitting a first ultrasonic shock wave having a first energy level and for emitting a second ultrasonic shock wave having a second energy level greater than the first energy level, the second ultrasonic shock wave being emitted to disintegrate a calculus after emission of the first ultrasonic shock wave;
   sound receiver means for receiving audio sounds from the living body and for transforming the audio sounds into electrical signals, said audio sounds being generated by the living body responsive to exposure to said first ultrasonic sound wave; and
   confirmation means, coupled to said sound receiver means, for determining whether the position of the calculus coincides with the focal point of the ultrasonic transducer means by analyzing the electrical signals received from said sound receiver means.

2. An apparatus according to claim 1 further comprising:
   control means coupled to said confirmation means and said ultrasonic transducer means for allowing the emission of the second ultrasonic shock wave when said confirmation means has determined that the position of the calculus coincident with the focal point of the ultrasonic transducer means.

3. An apparatus according to claim 2, wherein said confirmation means includes extracting means for extracting frequency components corresponding to the inherent frequency of audio sounds generated by the calculus in response to exposure to the first ultrasonic shock wave, and comparing means for comparing said extracted frequency components with a predetermined threshold value.

4. An apparatus according to claim 3, wherein said comparing means comprises means for generating a confirmation signal or a non-confirmation signal in accordance with the compared result, and the control means comprises means for allowing the emission of the second ultrasonic shock wave in response to the confirmation signal and exhibiting the emission of the second ultrasonic shock wave in response to the non-confirmation signal.

5. An apparatus according to claim 4, wherein said confirmation means further includes counter means for counting the number of times the non-confirmation signal is generated, and warning means for generating a warning signal when the non-confirmation signal is generated more than a predetermined number of times.

6. An apparatus according to claim 1 further comprising imaging means connected to the ultrasonci transducer means for generating a cross-sectional image of the living body and display means for displaying the cross-sectional image generated by said imaging means.

7. An ultrasonic lithotrity apparatus comprising:
   an ultrasoinc transducer having focal point for transmitting ultrasonic shock waves to a living body;
   drive means for driving said ultrasonic transducer to emit first ultrasonic shock waves for confirming that the focal point of the ultrasonic transducer is coincident with the position of a calculus in the living body and to emit second ultrasonic waves for disintegrating the calculus, the first ultrasonic shock waves having a lower energy level than the second ultrasonic shock waves;
   sound receiver means for receiving sounds from the living body and for converting the sounds into electrical signals, said sounds being generated by the living body responsive to exposure to said first ultrasonic shock waves; and
   confirmation means, coupled to said sound receiver means, for determining whether the calculus is positioned at the focal point of said ultrasonic transducer by analyzing the electrical signals produced by said sound receiver means.

8. An ultrasonic lithotrity apparatus according to claim 7 further comprising control means connected to said confirmation means and said drive means for allowing emission of the second ultrasonic shock wave when said confirmation means has determined that the calculus is positioned at the focal point of said ultrasonic transducer.

9. An ultrasonic lithotrity apparatus according to claim 8, wherein said means comprises means for allowing the emission of a plurality of second ultrasonic shock waves to the calculus.

10. An apparatus according to claim 7 further comprising imaging means connected to the ultrasonic transducer means for generating a cross-sectional image of the living body and display means for displaying the cross-sectional image generated by said imaging means.

11. A method for disintegrating a calculus in a living body comprising the steps of:

emitting a first shock wave at a focal point of a shock wave generator on the living body;

receiving sounds from the living body generated in response to the first shock wave;

comparing the level of the sounds with a threshold value to determine whether the calculus is at the focal point of the shock wave generator;

generating a first signal if the position of the calculus coincides with the focal point;

generating a second signal if the position of the calculus does not coincide with the focal point;

emitting a second shock wave at the focal point on the living body in response to the first signal to disintegrate the calculus; and inhibiting the emission of said second shock wave in response to the second signal.

* * * * *